United States Patent [19]

Klingler et al.

[11] 4,089,877
[45] May 16, 1978

[54] PROCESS FOR PRODUCING HYDROXYARYLPOLYMETHYLENESULFONIUM SALTS

[75] Inventors: Thomas C. Klingler; Donald L. Schmidt; Warner Jensen, Jr.; Demetrius Urchick, all of Midland, Mich.

[73] Assignee: The Dow Chemical Company, Midland, Mich.

[21] Appl. No.: 626,417

[22] Filed: Oct. 28, 1975

[51] Int. Cl.² .......................................... C07D 333/16
[52] U.S. Cl. .......................... 260/332.3 R; 260/329 S; 260/329 HS; 260/332.5
[58] Field of Search ...................... 260/332.3 R, 332.5, 260/329 S, 329 HS

[56] References Cited

U.S. PATENT DOCUMENTS

| 3,636,052 | 1/1972 | Hatch et al. | 260/332.3 R |
| 3,749,738 | 7/1973 | Hatch et al. | 260/332.3 R |

Primary Examiner—Bernard Helfin
Assistant Examiner—A. Siegel
Attorney, Agent, or Firm—L. Wayne White

[57] ABSTRACT

Compounds of the formula

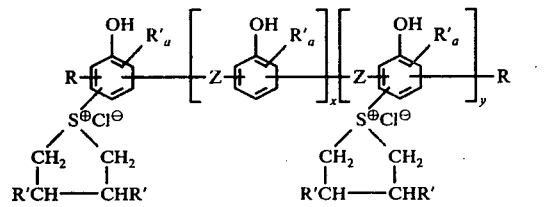

wherein:
  each R individually is H, OH or $C_1$-$C_4$ alkoxy;
  each R' individually is H or $C_1$-$C_4$ alkyl, and $a$ is 1 or 2;
  each sulfur is ortho or para to a phenolic oxygen;
  $x$ is 0 or a positive number;
  $y$ is 0 or a positive number;
  Z is a bridging group of the formula:
    (1) —O—, —S—, —O($C_mH_{2m}$)O— where $m$ is 1-6, and $\Sigma(x+y)=1$;
    (2) —CR''$_2$— where R'' is $C_1$-$C_4$ alkyl, and $\Sigma(x+y)=1$; or
    (3) —$CH_2$— and $\Sigma(x+y)=1$-20;
are produced in the process comprising the steps of:
  (a) reacting chlorine or sulfuryl chloride with a solution comprising a cyclic polymethylene sulfide (e.g. thiophane), iodine and HCl dissolved in liquid sulfur dioxide, thus forming a chlorine complex of the cyclic sulfide; and
  (b) reacting the chlorine complex from step (a) with the appropriate phenol in liquid sulfur dioxide.

16 Claims, No Drawings

4,089,877

PROCESS FOR PRODUCING HYDROXYARYLPOLYMETHYLENESULFONIUM SALTS

BACKGROUND OF THE INVENTION

The hydroxyarylsulfonium chlorides form a known class of compounds. These compounds are useful, for example, as surface active agents, biological toxicants, intermediates in the synthesis of organic derivatives, etc. The hydroxyarylpolymethylenesulfonium chlorides are particularly useful as intermediates to the preparation of the corresponding cyclic sulfonium zwitterions (which are water-soluble monomers).

Several methods have been previously used to prepare the hydroxyarylsulfonium chlorides.

U.S. Pat. No. 3,133,971 teaches, for example, that the hydroxyarylsulfonium chlorides can be prepared by reacting a sulfide (R—S—R') with a monophenol in the presence of chlorine at a reaction temperature of from about −50° to about 10° C. The patentee states that the reaction may optionally be conducted in a diluent, such as HCl, concentrated hydrochloric acid, phosphoric acid, alkyl halides, aromatic hydrocarbons, etc. This procedure is plagued, however, by side reactions involving chlorine and phenol which produce undesirable byproducts that are difficult to separate from the desired hydroxyarylsulfonium chloride.

U.S. Pat. No. 3,259,660 teaches a modification of the above reaction. The modification comprises conducting the reaction in two steps. In the first step, chlorine is added to the organic sulfide in a suitable diluent at a reaction temperature of between about −50° and about 10° C thus forming a chlorine complex with the organic sulfide. In the second step, the chlorine complex is added to the monophenol in the presence of a liquid diluent and the reaction mixture reacted under agitation at a temperature of from about −50° to about 20° C until the product is formed. Patentee states that this process is not particularly adaptable to reactions involving highly substituted phenols which may be sterically hindered.

U.S. Pat. Nos. 3,732,317; 3,772,391 and 3,775,485 likewise teach a two step process involving a chlorine complex with the sulfide. In these patents, an organic sulfide (R—S—R') is reacted with chlorine in the presence of sulfuric acid to form a chloro-sulfonium bisulfate of the formula (R—S(Cl)—R')⊕HSO₄⊖. The chloro-sulfonium bisulfate is then reacted with the monophenol to give the corresponding hydroxyarylsulfonium compound.

All of the above patents are limited to the reaction of monophenols with sulfides of the formula R—S—R'. Cyclic sulfides have been consistently omitted from the teachings of these patents.

The reaction of cyclic sulfides with a polyphenol is described, for example, in U.S. Pat. No. 3,767,622. There, patentee teaches that the poly(hydroxyarylpolymethylenesulfonium) salts can be formed in one of two methods. The first method involves reacting a polyphenol with a cyclic sulfide in the presence of chlorine at a temperature of from −40° to −8° C. The product yield from this process is said to be improved by adding anhydrous HCl to the cyclic sulfide prior to adding the polyphenol and chlorine. In the second process, a polyphenol and a polymethylenesulfoxide are condensed in the presence of a strong anhydrous acid, such as HCl. Low temperatures and Lewis acid catalysts (e.g. aluminum chloride, sulfur dioxide, etc.) are said to be useful in minimizing side reactions and improving the color.

SUMMARY OF THE INVENTION

A novel process has now been discovered for making hydroxyarylpolymethylenesulfonium salts of the formula

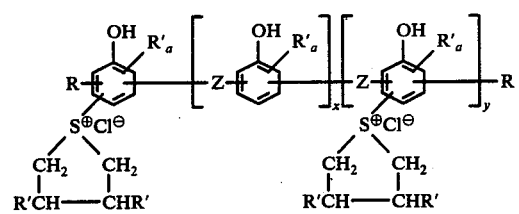

wherein:
each R individually is H, OH or $C_1$-$C_4$ alkoxy;
each R' individually is H or $C_1$-$C_4$ alkyl, and $a$ is 1 or 2;
each sulfur is ortho or para to a phenolic oxygen;
$x$ is 0 or a positive number;
$y$ is 0 or a positive number;
Z is a bridging group of the formula:
 (1) —O—, —S—, —O($C_mH_{2m}$)O— where $m$ is 1–6, and $\Sigma(x+y)=1$;
 (2) —CR''$_2$— where R'' is $C_1$-$C_4$ alkyl, and $\Sigma(x+y)=1$; or
 (3) —$CH_2$— and $\Sigma(x+y)=1$–20.

The novel process comprises the steps of:
(a) reacting by contacting chlorine ($Cl_2$) or sulfuryl chloride ($SO_2Cl_2$) with a solution comprising a cyclic polymethylene sulfide of the formula

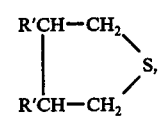

wherein R' has the above meaning, iodine and HCl dissolved in liquid sulfur dioxide, thus forming a chlorine complex of the cyclic sulfide; and (b) reacting by contacting in liquid sulfur dioxide the chlorine complex from step (a) with a phenol of the formula

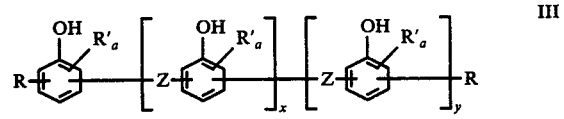

where R, R', $a$, $x$, $y$ and $z$ have the above meanings.

The new process produces the desired product in excellent yield and purity and is particularly effective in the reaction of highly substituted phenols or sterically-hindered phenols with the cyclic sulfides.

DETAILED DESCRIPTION OF THE INVENTION

Step (a)

In this step, a chlorine complex of the cyclic sulfide is formed by reacting by contacting chlorine or sulfuryl chloride with a solution comprising four essential ingredients:

(1) a cyclic polymethylenesulfide of the formula

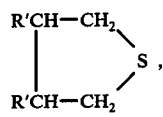

wherein each R' individually is hydrogen or $C_1$–$C_4$ alkyl (preferably each R' is hydrogen);
(2) iodine ($I_2$) in minor amounts;
(3) HCl; and
(4) liquid sulfur dioxide as the reaction medium.
The chlorine complex of the cyclic sulfide is believed to correspond to the formula

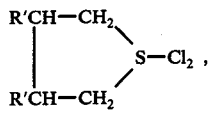

wherein R' has the above meaning. This structure would be consistent with the structure assigned to chlorine and bromine complexes of thiophane by Wilson et al., J. Org. Chem., Vol. 38, No. 12, 2156 (1973). Step (a) is believed to be a unique process for forming such chlorine complexes of cyclic sulfides.

Wilson et al. reported that the chlorine/thiophane complex decomposed in the presence of water to form the corresponding sulfoxide(s). In our work, it was observed that the chlorine/cyclic sulfide complex formed in liquid sulfur dioxide also decomposed in the presence of even minor amounts of water to form cyclic sulfoxides. Even the small amounts of water which dissolved or entrained in the reactants and/or present in the reaction equipment was sufficient to cause serious hydrolytic degradation of the complex. This was a serious problem since the by-products of this degradation were extremely malodorous, difficult to remove, and lowered the product yield by consuming the expensive cyclic sulfide reactant. We discovered that iodine inhibited or prevented the formation of such cyclic sulfoxides. This obviated the need to go to extremes in establishing and maintaining an absolutely anhydrous system in preparation of the complex. This was an important discovery, from a commercial standpoint. The iodine seems to be unusually effective in inhibiting the cyclic sulfoxide formation. Thus, iodine is added in only small amounts of, for example, up to about 0.002 moles of iodine or less per mole of cyclic sulfide.

It has also been observed that the chlorine/cyclic sulfide complex in liquid $SO_2$ can also decompose to form minor (but significant) amounts of two highly toxic compounds represented by formulas IV and V

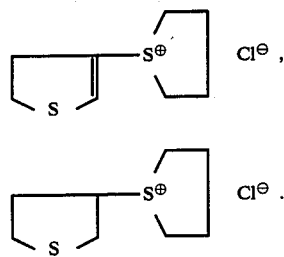

The mechanism(s) by which such toxins are produced is not completely understood. However, the formation of such toxins is eliminated or substantially eliminated by the presence of HCl in the reaction mixture. The amount of HCl may be varied from minor amounts up to saturation of the solution with HCl. From an operating standpoint, it is most convenient to merely bubble anhydrous gaseous HCl into the sulfur dioxide solution until the solution is saturated or essentially saturated with HCl.

Step (a) may be conducted at any convenient temperature and pressure so long as the reaction mixture is a liquid and the chlorine/cyclic sulfide complex is not thermally decomposed. Reaction temperatures of from about $-50°$ to about $10°$ C are generally suitable but reaction temperatures of from about $-30°$ to about $-8°$ are preferred. The reaction mixture boils at about $-8°$ C under atmospheric pressure and this represents a very satisfactory means of controlling the reaction temperature.

Step (b)

This step is conducted by contacting in liquid sulfur dioxide the chlorine/cyclic sulfide complex from step (a) with a phenol of the formula

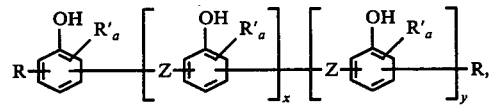

where R, R', $a$, $x$, $y$ and Z have the above meanings. This step may likewise be conducted at any convenient temperature and pressure so long as the reaction mixture is liquid and the reactants are not thermally decomposed. However, reaction temperatures of from about $-50°$ to about $10°$ C are normally used and reaction temperatures of from about $-30°$ to about $-8°$ C are again preferred. Further, we prefer to conduct this step in the presence of a small but catalytic amount of a Lewis acid (e.g. $BF_3$, $AlCl_3$, etc) with $BF_3$ and $AlCl_3$ being the Lewis acid catalysts of choice ($BF_3$ is the most preferred species).

The phenols used in the instant process are also a known class of compounds and they have been previously used in preparing the hydroxyarylpolymethylenesulfonium chlorides. For example, any of the phenols used in U.S. Pat. Nos. 3,749,737; 3,749,739 and the above-mentioned patents which correspond to formula III above can be suitably used herein. The most preferred phenols are 4,4'-isopropylidenediphenol and the phenol-formaldehyde condensation products known as novolac resins. The novolac resins correspond to formula III above wherein R and R' are each hydrogen, and Z is represented by group (3). The hydroxyarylpolymethylenesulfonium chloride salts prepared from these preferred polyphenols are particularly useful as intermediates in making the corresponding sulfonium zwitterions which are extremely useful water-soluble coatings.

The ratio of reactants in the instant process may be varied to convenience but the stoichiometry of the reaction requires one mole of chlorine per mole of cyclic sulfide in Step 1 and one mole on the chlorine/cyclic sulfide complex per hydrogen atom to be replaced on the phenol in step (b). We normally prefer to use a slight excess of cyclic sulfide in step (a) and a slight excess of the chlorine/cyclic sulfide complex in step (b).

The product, as it is obtained from step (b), is obtained as a solution in liquid sulfur dioxide. If desired, the product may be recovered as a water solution thereof by the following steps:

Step (c), add water to the reaction mixture from step (b) in an amount at least sufficient to dissolve the sulfonium product;

Step (d) remove the sulfur dioxide as a volatile gas from the reaction mixture from step (c). This is done by merely warming the mixture to about room temperature (preferably under reduced pressure).

Step (e) extract the aqueous solution from step (d) with a water-immiscible organic solvent to remove organic impurities and/or unreacted starting materials. A wide variety of conventional organic solvents can be used and include, for example, chloroform, methylene chloride, ethyl acetate, hexanol, etc. Of these, hexanol is the preferred solvent.

Step (f) isolate the water layer from step (e). This is the aqueous solution of the desired sulfonium chloride product.

The sulfonium zwitterions can be prepared directly from the aqueous solution in step (f) by passing the aqueous solution over a conventional anion exchange resin. This is a conventional technique for forming the sulfonium zwitterions.

The following examples will further illustrate the invention.

EXPERIMENTAL

EXAMPLE 1

A 12 liter flask was charged with 1675 g of thiophane and 5597 g of liquid sulfur dioxide. HCl (180 g) was sparged into the reaction mixture and 200 mg of iodine added. To this reaction mixture was added dropwise, with stirring, 2429.5 g of sulfuryl chloride at a reaction temperature of between −19° and −15° C. After this addition was complete, bisphenol-A (1712 g) and BF$_3$ (30 g) was added. After 2.5 hours at −15° C, 5 liters of water were added incrementally while the sulfur dioxide was removed under reduced pressure. The resulting solution was extracted with approximately 8 liters of hexanol. The desired product was thus obtained in high yield and purity as an aqueous solution. The aqueous solution of the product was of excellent color, and a negligible amount of the toxins represented by formulas IV and V above.

The corresponding cyclic sulfonium zwitterion was easily prepared by passing the aqueous solution of the above product over a Dowex-2® resin in the OH form.

EXAMPLE 2

In like manner, liquid sulfur dioxide (300 g), iodine (10 mg), thiophene (98.7 g) and HCl (93 g) were charged to a suitable reaction vessel and the temperature adjusted to −20° C. To this stirred solution was added sulfuryl chloride (148.6 g). When the addition of sulfuryl chloride was complete, p-cresol (108.1 g) and BF$_3$ (3 g) were added. The reaction mixture was maintained at reflux temperature for 1 hour. The sulfur dioxide was then removed under reduced pressure and agitation continued for approximately 10 minutes. Water (approximately 250 ml) was added with stirring. The reaction mixture was extracted 3 times with 250 ml portions of chloroform and the desired sulfonium chloride precipitated by dripping the water solution into acetone. The sulfonium chloride product was thus recovered as a white crystalline solid in approximately 73% of theoretical yield, based on the reactants charged.

We claim:

1. A process for making a hydroxyarylpolymethylenesulfonium salt of the formula

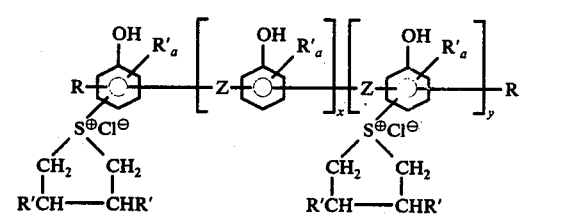

wherein:
each R individually is H, OH or C$_1$-C$_4$ alkoxy;
each R' individually is H or C$_1$-C$_4$ alkyl, and $a$ is 1 or 2;
each sulfur is ortho or para to a phenolic oxygen;
$x$ is 0 or a positive number;
$y$ is 0 or a positive number;
Z is a bridging group of the formula:
(1) —O—, —S—, —O(C$_m$H$_{2m}$)O— where $m$ is 1-6, and $\Sigma(x+y)=1$;
(2) —CR''$_2$— where R'' is C$_1$-C$_4$ alkyl, and $\Sigma(x+y)=1$; or
(3) —CH$_2$— and $\Sigma(x+y)=1$-20;
said process comprising the steps of:
(a) reacting by contacting chlorine or sulfuryl chloride with a solution comprising (1) a cyclic polymethylene sulfide of the formula

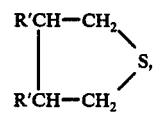

wherein R' has the above meaning,
(2) a small but sufficient amount of iodine to inhibit the formation of cyclic sulfoxides, and (3) HCl dissolved in (4) liquid sulfur dioxide, thus forming a chlorine complex of the cyclic sulfide; and
(b) reacting by contacting in liquid sulfur dioxide the chlorine complex from step (a) with a phenol of the formula

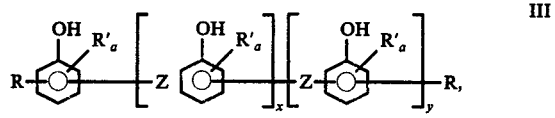

where R, R', $a$, $x$, $y$ and Z have the above meanings.

2. The process defined by claim 1 wherein the solution of step (a) is saturated or essentially saturated with HCl prior to contacting same with chlorine or sulfuryl chloride.

3. The process defined by claim 1 in which step (a) is conducted at a reaction temperature of from about −8° to about −30° C.

4. The process defined by claim 1 in which step (b) is conducted in the presence of a small but catalytic amount of a Lewis acid.

5. The process defined by claim 4 in which said Lewis acid is BF$_3$ or AlCl$_3$.

6. The process defined by claim 5 in which said Lewis acid is $BF_3$.

7. The process defined by claim 4 in which step (b) is conducted at a reaction temperature of from about $-8°$ to about $-30°$ C.

8. The process defined by claim 1 in which said polyphenol is bisphenol A or a novolac resin.

9. The process defined by claim 1 which comprises the additional steps of:
    (c) adding water to the reaction mixture from step (b) in an amount at least sufficient to dissolve the sulfonium product;
    (d) removing sulfur dioxide as a volatile gas from the reaction mixture from step (c);
    (e) extracting the aqueous solution from step (d) with a water immiscible organic solvent to remove organic impuritites and/or unreacted starting materials; and
    (f) recovering the desired sulfonium product as an aqueous solution thereof.

10. The process defined by claim 1 in which step (a) is conducted by reacting by contacting, at a reaction temperature of from about $-8°$ to about $-30°$ C, chlorine or sulfuryl chloride with a solution of thiophane, iodine and liquid sulfur dioxide saturated or essentially saturated with HCl, thus forming a chlorine complex of the thiophane; and step (b) is conducted by reacting by contacting the chlorine complex from step (a) with bisphenol A or a novolac resin in the presence of $BF_3$ of $AlCl_3$ in liquid sulfur dioxide at a reaction temperature of from about $-8°$ to about $-30°$ C.

11. The process defined by claim 10 which comprises the additional steps of:
    (c) adding water to the reaction product of step (b) in an amount at least sufficient to dissolve the sulfonium product;
    (d) removing sulfur dioxide as a volatile gas;
    (e) extracting the aqueous solution from step (d) with chloroform, methylene chloride, ethyl acetate or hexanol to thereby remove organic impurities and/or unreacted starting materials; and
    (f) recovering the desired sulfonium product as an aqueous solution thereof.

12. A method of preparing a chlorine complex of cyclic sulfides comprising reacting by contacting chlorine or sulfuryl chloride with a solution comprising (1) a cyclic polymethylene sulfide of the formula

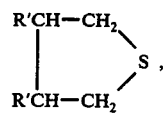

wherein R' is H or $C_1$-$C_4$ alkyl,
(2) a small but sufficient amount of iodine to inhibit the the formation of cylic sulfoxides, and (3) HCl dissolved in (4) liquid sulfur dioxide.

13. The process defined by claim 12 wherein said cyclic sulfide is thiophane.

14. The process defined by claim 12 wherein the reaction temperature is from about $-8°$ to about $-30°$ C.

15. The process defined by claim 1 wherein Steps (a) and (b) are each individually conducted at a reaction temperature of from about $-50°$ to $10°$ C.

16. The process defined by claim 1 wherein said iodine is present in an amount up to about 0.002 moles of iodine per mole of cyclic polymethylene sulfide.

* * * * *